(12) United States Patent
Anslyn et al.

(10) Patent No.: US 8,637,323 B2
(45) Date of Patent: Jan. 28, 2014

(54) FLUORESCENT NITRIC OXIDE PROBES AND ASSOCIATED METHODS

(71) Applicant: Board of Regents, The University of Texas System, Austin, TX (US)

(72) Inventors: Eric V. Anslyn, Austin, TX (US); Youjun Yang, Austin, TX (US); Michelle M. Adams, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/645,217

(22) Filed: Oct. 4, 2012

(65) Prior Publication Data

US 2013/0302903 A1     Nov. 14, 2013

Related U.S. Application Data

(63) Continuation of application No. PCT/US2011/032226, filed on Apr. 13, 2011.

(60) Provisional application No. 61/326,750, filed on Apr. 22, 2010.

(51) Int. Cl.
*G01N 33/00*     (2006.01)
*G01N 21/76*     (2006.01)

(52) U.S. Cl.
USPC ........... 436/116; 436/106; 436/172; 514/740; 514/741; 252/408.1

(58) Field of Classification Search
USPC .......... 436/106, 116, 164, 166, 172; 514/740, 514/741; 252/408.1
See application file for complete search history.

(56) References Cited

U.S. PATENT DOCUMENTS

| | | | | |
|---|---|---|---|---|
| 7,494,821 | B2 * | 2/2009 | Lippard et al. | 436/172 |
| 8,465,985 | B2 * | 6/2013 | Nagano et al. | 436/172 |
| 2009/0055939 | A1 * | 2/2009 | Umezawa et al. | 800/3 |
| 2011/0098475 | A1 * | 4/2011 | Nagano et al. | 546/256 |

OTHER PUBLICATIONS

Bryan et al. Methods to detect nitric oxide and its metabolites in biological samples. Free Radic Bioi Med 2007, 43:p. 645-657; p. 6, para 2, Fig 2.

Smith et al. Conjugated polymer-based fluorescence turn-on sensor for nitric oxide. Org Lett 2005, 7:3573-3575; abstract.

Ouyang et al. Bioimaging nitric oxide in activated macrophages in vitro and hepatic inflammation in vivo based on a copper-naphthoimidazol coordination compound. Nitric Oxide 2008, 19:42-49; abstract, p. 45, Fig. 2.

Nagano. Bioimaging probes for reactive oxygen species and reactive nitrogen species. J Clin Biochem Nutr 2009, 45 (2):111-124; p. 116, Fig 6.

Yang et al. A highly selective low-background fluorescent imaging agent for nitric oxide. J Am Chern Soc Jul. 30, 2010,132:13114-13116.

\* cited by examiner

*Primary Examiner* — Maureen Wallenhorst
(74) *Attorney, Agent, or Firm* — Robert R. Riddle; Reed Smith LLP

(57) ABSTRACT

Nitric oxide probes including a compound represented by Formula, I, II, III, IV, V, VI or a combination thereof are provided. Methods of using these nitric oxide probes to detect nitric oxide are also provided.

3 Claims, 5 Drawing Sheets

FLUORESCENT NITRIC OXIDE PROBES AND ASSOCIATED METHODS

CROSS REFERENCE TO RELATED APPLICATIONS

This application is a continuation of PCT/US11/32226, filed Apr. 13, 2011 and claims priority to U.S. Provisional Application No. 61/326,750, filed Apr. 22, 2010, both of which are incorporated herein by reference.

BACKGROUND

The biological roles of nitric oxide (NO) have led chemists and molecular biologists to seek cellular imaging agents responsive to this species. The creation of such agents derives from the pivotal role of NO in vasodilation as an endothelial-derived relaxing factor (EDRF), and its function as a platelet aggregation inhibitor, neurotransmitter, antimicrobial agent, and due to its antitumor activity in cardiovascular, nervous, and immune systems. Although a variety of quantification techniques have been developed, fluorescence techniques are the most desirable because of their sensitivity, and high spatiotemporal resolution when combined with microscopy. Consequently, a number of fluorescent NO probes are available, but each is hampered by certain selectivity and/or synthetic limitations.

Currently, the most common approach for NO detection involves the use of ortho-diamino aromatics under aerobic conditions, which reacts with $NO^+$ equivalent, presumably $N_2O_3$ to furnish fluorescent triazole derivatives. Turn-on fluorescence signals are achieved due to suspension of photoinduced electron transfer (PET). Examples using fluoresceins (such as DAF-2 DA), anthraquinones, rhodamines (such as DAR-4M AM), BODIPYs, and cyanines are documented. Such probes are among the current state of the art, yet severe limitations exist. First of all, in the presence of $H_2O_2$/peroxidase, $OONO^-$, $OH.$, $NO_2.$, and $CO_3.^-$, the intrinsically electron rich diaminobenzene moiety is easily oxidized to an arylaminyl radical, which combines with NO and leads to triazoles. Second, dehydroascorbic acid (DHA) condenses with ortho-diamino aromatics and turns on the fluorescence of such probes. It was reported that 1 mM DHA yielded a fluorescence signal with the commercial NO probes DAF-2 DA, DAR-4M AM, comparable to 300 nM and 100 µM of NO respectively. Third, benzotriazoles are pH sensitive ($pK_a$'s≈6.69) near neutral pH. The pH sensitivity can be solved by methylation of one of the amines, however the reactivity of the probe toward DHA was undesirably enhanced.

The aforementioned limitations complicate NO detection using ortho-diamines. Hence, a series of metal ligand complexes for NO detection are also currently under development. For example, $Cu^{II}(FL_5)$, displays a fluorescence enhancement upon exposure to NO and can be used as a cellular imaging agent. However, given a dissociation constant ($K_d$) of 1.5 µM and the presence other metal ions in physiological conditions, it is a concern that the complex will release cytotoxic $Cu^{2+}$. Complexes with lower $K_d$'s were reported, though with decreased reactivity toward NO.

Most recently, single-walled carbon nanotubes (SWCN) wrapped with 3,4-diaminophenyl-functionalized dextrans were used for in vitro or in vivo studies. The NIR fluorescence of the SWCN is bleached by several reactive oxygen/nitrogen species, but at least NO does so more than others.

SUMMARY

The present disclosure generally relates to nitric oxide probes. More particularly, the present disclosure relates to fluorescent nitric oxide probes and associated methods.

The present disclosure provides a nitric oxide probe that may be used to detect and/or image NO and associated methods. In one embodiment, a nitric oxide probe of the present disclosure comprises a compound that is represented by the following Formula I:

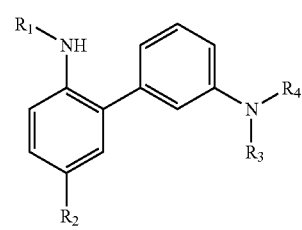

Formula I wherein $R_1$ is an alkyl group or H, $R_2$ is H, CN, $SO_3^-$, sulfamoyl, alkyl substituted sulfamoyls, $COO^-$, carbamoyl, alkyl substituted carbamoyls, $R_3$ is an alkyl group, and $R_4$ is an alkyl group.

In another embodiment, a nitric oxide probe of the present disclosure comprises a compound that is represented by the following Formula II:

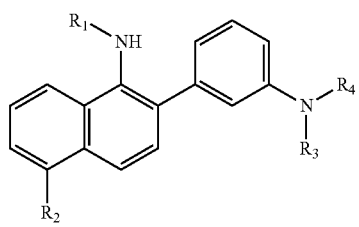

Formula II wherein $R_1$ is an alkyl group or H, $R_2$ is H, CN, $SO_3^-$, sulfamoyl, alkyl substituted sulfamoyls, $COO^-$, carbamoyl, alkyl substituted carbamoyls, $R_3$ is an alkyl group, and $R_4$ is an alkyl group. In one particular embodiment, wherein $R_1$ is H, $R_2$ is CN, $R_3$ is an methyl group, and $R_4$ is an methyl group, the compound is referred to as $NO_{550}$.

In yet another embodiment, a nitric oxide probe of the present disclosure comprises a compound that is represented by the following Formula III:

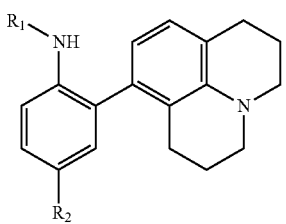

Formula III wherein $R_1$ is an alkyl group or H and $R_2$ is H, CN, $SO_3^-$, sulfamoyl, alkyl substituted sulfamoyls, $COO^-$, carbamoyl, alkyl substituted carbamoyls.

In yet another embodiment, a nitric oxide probe of the present disclosure comprises a compound that is represented by the following Formula IV:

Formula IV wherein $R_1$ is an alkyl group or H and $R_2$ is H, CN, $SO_3^-$, sulfamoyl, alkyl substituted sulfamoyls, $COO^-$, carbamoyl, alkyl substituted carbamoyls.

In yet another embodiment, a nitric oxide probe of the present disclosure comprises a compound that is represented by the following Formula V:

Formula V wherein $R_1$ is an alkyl group or H, $R_2$ is H, CN, $SO_3^-$, sulfamoyl, alkyl substituted sulfamoyls, $COO^-$, carbamoyl, alkyl substituted carbamoyls and $R_3$ is an alkyl group or H.

In yet another embodiment, a nitric oxide probe of the present disclosure comprises a compound that is represented by the following Formula VI:

Formula VI wherein $R_1$ is an alkyl group or H, $R_2$ is H, CN, $SO_3^-$, sulfamoyl, alkyl substituted sulfamoyls, $COO^-$, carbamoyl, alkyl substituted carbamoyls and $R_3$ is an alkyl group or H.

The features and advantages of the present invention will be readily apparent to those skilled in the art upon a reading of the description of the embodiments that follows.

DRAWINGS

Some specific example embodiments of the disclosure may be understood by referring, in part, to the following description and the accompanying drawings.

Figure 5:
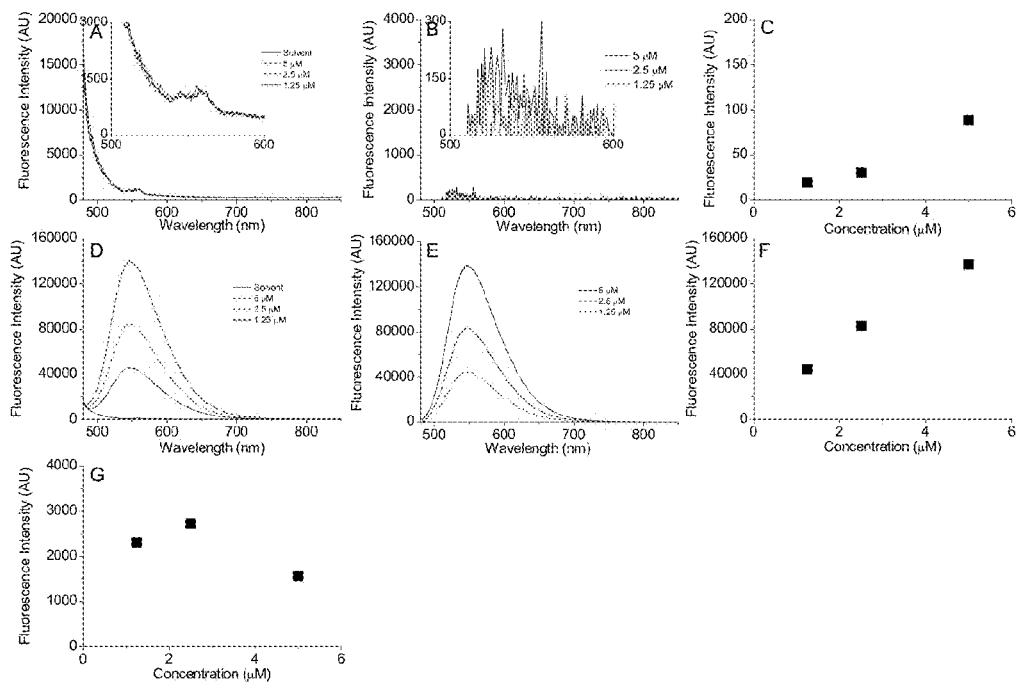

FIG. 5A is a graph depicting the emission spectra of the 20% DMSO in PBS buffer (50 mM at pH 7.4 with 150 mM NaCl) and emission spectra of $NO_{550}$ at 5 μM, 2.5 μM, and 1.25 μM respective. The excitation wavelength is 470 nm.

FIG. 5B is a graph depicting the emission spectra of $NO_{550}$ at various concentrations corrected with the solvent background.

FIG. 5C is a graph depicting the averaged fluorescence intensity of $NO_{550}$ in the range of 447 nm to 553 nm with excitation wavelength at 470 nm.

FIG. 5D is a graph depicting the emission spectra of the 20% DMSO in PBS buffer (50 mM at pH 7.4 with 150 mM NaCl) and emission spectra of $AZO_{550}$ at 5 μM, 2.5 μM, and 1.25 μM respective. The excitation wavelength is 470 nm.

FIG. 5E is a graph depicting the emission spectra of $AZO_{550}$ at various concentrations corrected with the solvent background.

FIG. 5F is a graph depicting the fluorescence intensity of $AZO_{550}$ at 550 nm with excitation wavelength at 470 nm.

FIG. 5G is a graph depicting the ratio between the emission intensity of $AZO_{550}$ and $NO_{550}$ at 550 nm with excitation wavelength at 470 nm.

Figure 6:
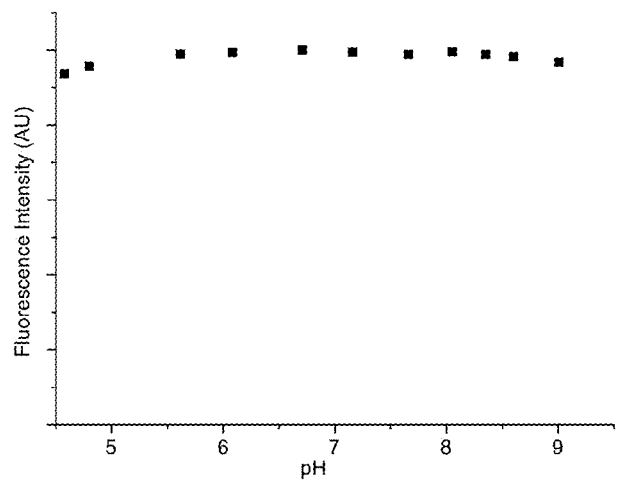

FIG. 6 is a graph depicting the pH dependence of the fluorescence intensity of $AZO_{550}$.

Figure 7:
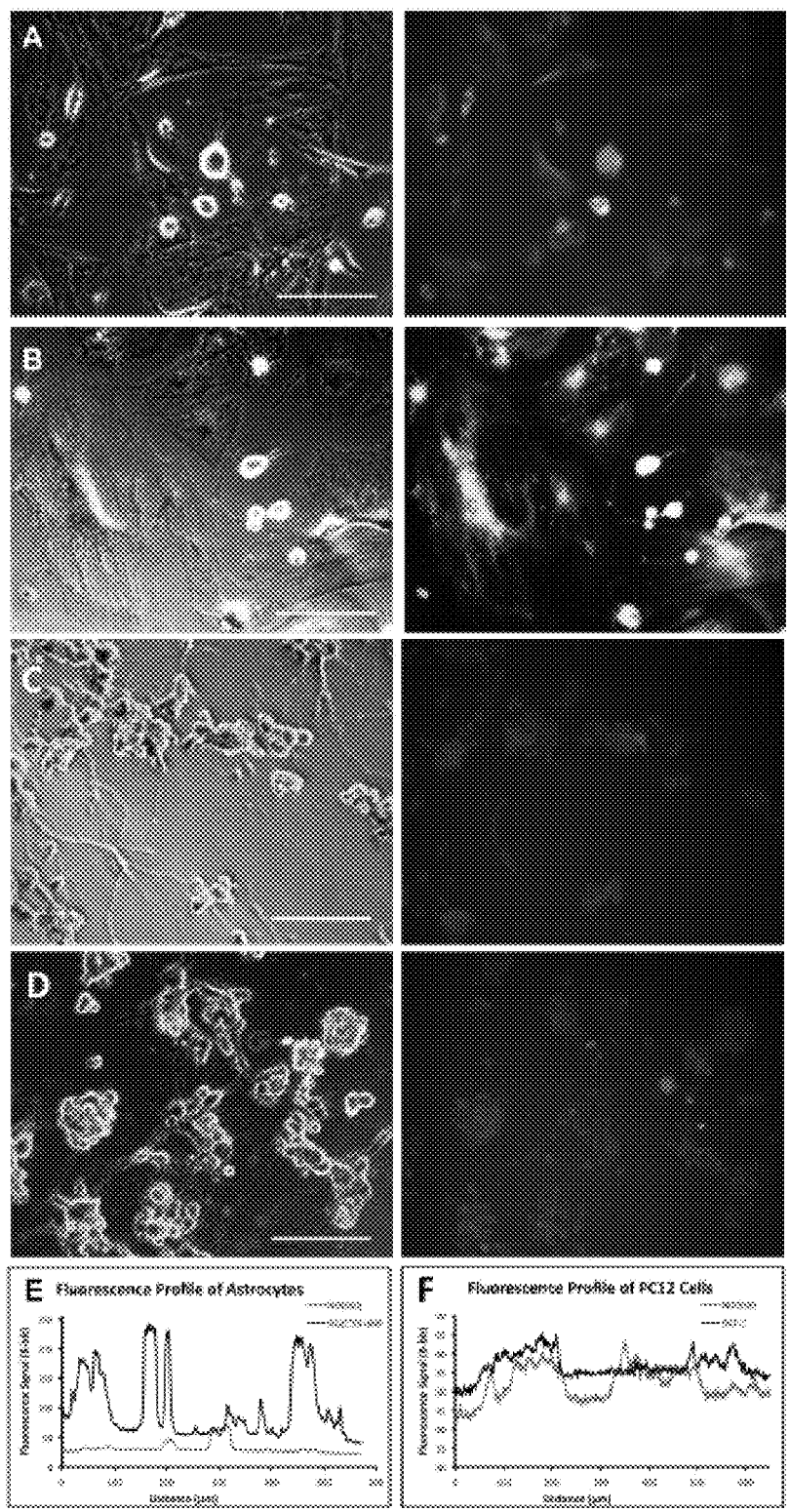

FIG. 7A is a phase contrast image (left) and corresponding wide-field fluorescence image (right) of neonatal spinal astrocytes stimulated with IFN-γ and IL-1β and incubated with 10 μM $NO_{550}$. Scale bar=150 μm. Linear levels were adjusted using Adobe Photoshop to aide in visualization.

FIG. 7B is a phase contrast image (left) and corresponding wide-field fluorescence image (right) of astrocytes treated identically to those in FIG. 7A, except with the addition of 1 mM SNP. Scale bar=150 μm. Linear levels were adjusted using Adobe Photoshop to aide in visualization.

FIG. 7C is a phase contrast image (left) and corresponding wide-field fluorescence image (right) of NGF-stimulated PC-12 cells incubated with 10 μM $NO_{550}$. Scale bar=150 μm. Linear levels were adjusted using Adobe Photoshop to aide in visualization.

FIG. 7D is a phase contrast image (left) and corresponding wide-field fluorescence image (right) of NGF-stimulated PC-12 cells and imaged 10 μM DAF-2 DA. Scale bar=150 μm. Linear levels were adjusted using Adobe Photoshop to aide in visualization.

FIG. 7E is a plot of fluorescence signal from raw images of astrocytes in FIGS. 7A and 7B. The plot represents a linescan constructed through the center (x-axis) of the images.

FIG. 7F is a plot of fluorescence signal from raw images of PC-12 cells in FIGS. 7C and 7D. The plot represents a linescan constructed through the center (x-axis) of the images.

FIG. 8A-D depicts the imaging of NO using $NO_{550}$ at various concentrations in PC12 cells.

The patent or application file contains at least one drawing executed in color. Copies of this patent or patent application publication with color drawing(s) will be provided by the Office upon request and payment of the necessary fee.

While the present disclosure is susceptible to various modifications and alternative forms, specific example embodiments have been shown in the figures and are described in more detail below. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to nitric oxide probes. More particularly, the present disclosure relates to fluorescent nitric oxide probes and associated methods.

The present disclosure provides a nitric oxide probe that may be used to detect and/or image NO. In one embodiment, a nitric oxide probe of the present disclosure comprises a compound that is represented by the following Formula I:

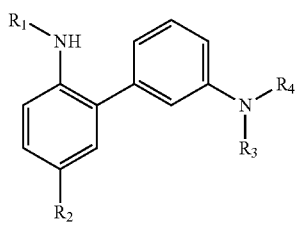

Formula I wherein $R_1$ is an alkyl group or H, $R_2$ is H, CN, $SO_3^-$, sulfamoyl, alkyl substituted sulfamoyls, $COO^-$, carbamoyl, alkyl substituted carbamoyls $R_3$ is an alkyl group, and $R_4$ is an alkyl group.

In another embodiment, a nitric oxide probe of the present disclosure comprises a compound that is represented by the following Formula II:

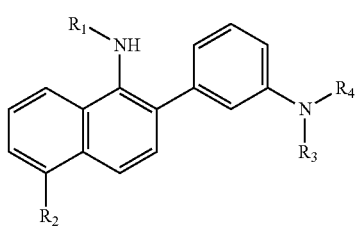

Formula II wherein $R_1$ is an alkyl group or H, $R_2$ is H, CN, $SO_3^-$, sulfamoyl, alkyl substituted sulfamoyls $COO^-$, carbamoyl, alkyl substituted carbamoyls, $R_3$ is an alkyl group, and $R_4$ is an alkyl group. In one particular embodiment, wherein $R_1$ is H, $R_2$ is CN, $R_3$ is a methyl group, and $R_4$ is a methyl group, the compound is referred to as $NO_{550}$.

In another embodiment, a nitric oxide probe of the present disclosure comprises a compound that is represented by the following Formula III:

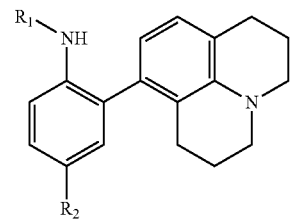

Formula III wherein $R_1$ is an alkyl group or H and $R_2$ is H, CN, $SO_3^-$, sulfamoyl, alkyl substituted sulfamoyls, $COO^-$, carbamoyl, alkyl substituted carbamoyls.

In another embodiment, a nitric oxide probe of the present disclosure comprises a compound that is represented by the following Formula IV:

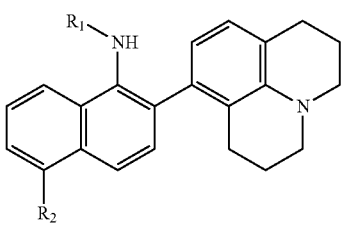

Formula IV wherein $R_1$ is an alkyl group or H and $R_2$ is H, CN, $SO_3^-$, sulfamoyl, alkyl substituted sulfamoyls, $COO^-$, carbamoyl, alkyl substituted carbamoyls.

In another embodiment, a nitric oxide probe of the present disclosure comprises a compound that is represented by the following Formula V:

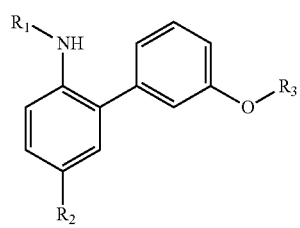

Formula V wherein $R_1$ is an alkyl group or H and $R_2$ is H, CN, $SO_3^-$, sulfamoyl, alkyl substituted sulfamoyls, $COO^-$, carbamoyl, alkyl substituted carbamoyls and $R_3$ is an alkyl group or H.

In another embodiment, a nitric oxide probe of the present disclosure comprises a compound that is represented by the following Formula VI:

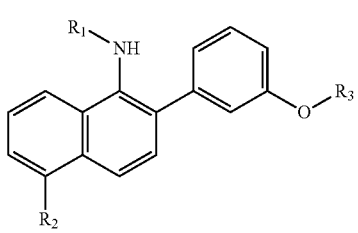

Formula VI wherein $R_1$ is an alkyl group or H and $R_2$ is H, CN, $SO_3^-$, sulfamoyl, alkyl substituted sulfamoyls, $COO^-$, carbamoyl, alkyl substituted carbamoyls and $R_3$ is an alkyl group or H.

While not wishing to be bound to any particular theory, it is believed that upon introduction of nitric oxide under aerobic conditions to a nitric oxide probe of the present disclosure, a nitrosation reaction occurs to yield a nitrosamine, which is subsequently scavenged via an electronic aromatic substitution reaction. The product of this reaction has an extended conjugation system in comparison to the initially synthesized compound and displays red shifted spectral properties, which are easily detected through fluorescence.

One of the many advantages of the present disclosure, many of which are not discussed herein, is that the nitric oxide probes of the present disclosure are highly selective and have not been found to interfere with reactive oxygenated species, reactive nitrogen species, ascorbic acid (AA), and dehydroascorbic acid (DHA). The probes of the present disclosure have also been shown to successfully respond to nitric oxide within cellular media. Due to the various roles of nitric oxide in the body, a sensing method utilizing a nitric oxide probe of the present disclosure can be applied to study any of the biological pathways where nitric oxide may be involved. In addition to the advantage of high specificity, a nitric oxide probe of the present disclosure is also advantageous due to its facile synthesis, low pH dependence, and fast reaction kinetics.

In one embodiment, a method of the present disclose comprises contacting a sample with a nitric oxide probe comprising a compound represented by Formula I-VI, or a combination thereof, and detecting emitted fluorescence from the nitric oxide probe. In some embodiments, the detection of emitted fluorescence involves the detection of a turn on fluorescence signal from a dark background at the longer wavelength upon nitric oxide addition, rather than a fluorescent signal fluctuation from a non-zero background seen by most nitric oxide detecting systems. Highly electron rich ortho-diamino aromatics were avoided so as to impede general oxidation by other reactive oxygen/nitrogen species and condensation with ascorbic acid (AA) analogs. In some embodiments, a spectrofluorometer may be used to detect emitted fluorescence from a nitric oxide probe.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

EXAMPLES

Figure 1:
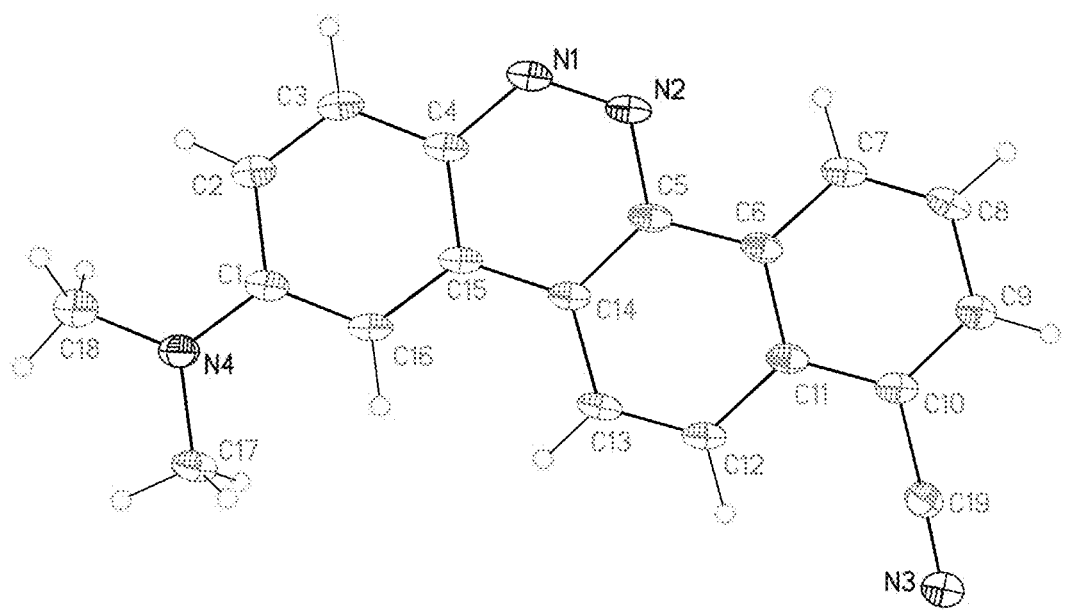
FIG. 1 is an ortep drawing of $AZO_{550}$.

NO gas was bubbled into a solution of $NO_{550}$ in $CH_2Cl_2$. A color change from light yellow to deep red was observed spontaneously. This phenomenon qualitatively demonstrated that $NO_{550}$ is reactive toward $NO/N_2O_3$, and the structure of the product ($AZO_{550}$) was unambiguously established via NMR, MS, and X-ray crystallography (FIG. 1). The ring closure occurs para to the dimethylamino group, not ortho, presumably due to steric hindrance. The schematic illustration below depicts $NO_{550}$ and the stepwise route to $AZO_{550}$.

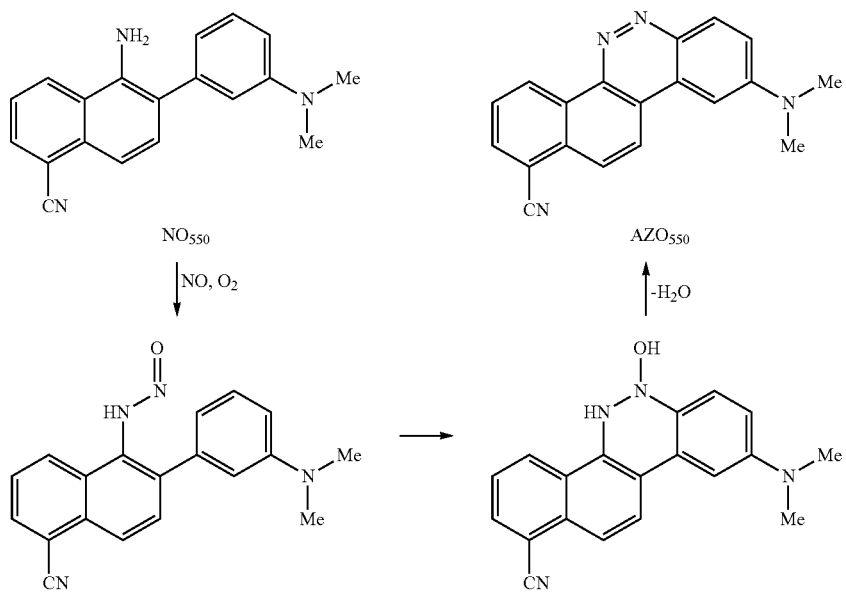

Figure 2:
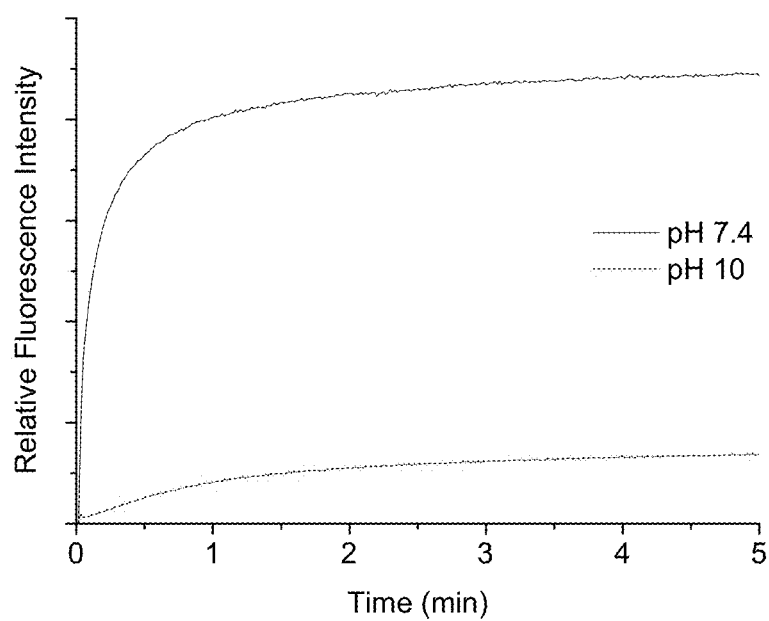
FIG. 2 is a graph depicting the kinetic profiles of the reactions between $NO_{550}$ (10 μM) and NO (0.6 eq) at pH 7.4 (PBS buffer with 20% DMSO 50 mM) and pH 10 (carbonate buffer with 20% DMSO, 50 mM).

The reaction between $NO_{550}$ and NO requires an $NO^+$ equivalent, such as $N_2O_3$. The reaction resembles the synthesis of azo compounds via a diazotization/coupling sequence. However, a profound difference exists. Diazotization occurs in acidic media to form diazonium salts from nitrosamines. However, the reaction between $NO_{550}$ and NO occurs rapidly at neutral (pH=7.4, vide infra) or even basic (pH=10, FIG. 2) aqueous conditions, where conversion of the initially formed nitrosamine derivative to a corresponding diazonium salt via acid-catalyzed dehydration is unlikely. This implies that electrophilic aromatic substitution on the electron deficient nitrosamine occurs to yield a hydroxyhydrazine derivative. Elimination of $H_2O$ would lead to the formation of $AZO_{550}$. The lower intensity with the experiment at pH 10 compared to that at pH 7.4 may be attributed to a combination of the following factors: 1) reaction is slower, and 2) hydrolysis of $N_2O_3$ at higher pH is accelerated.

Figure 3:
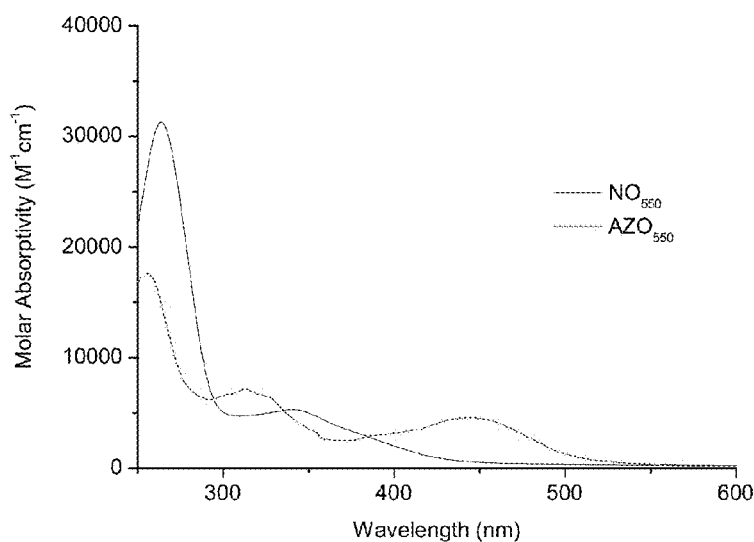
FIG. 3 is a graph depicting the absorption spectra of $NO_{550}$ and $AZO_{550}$.
Figure 4:
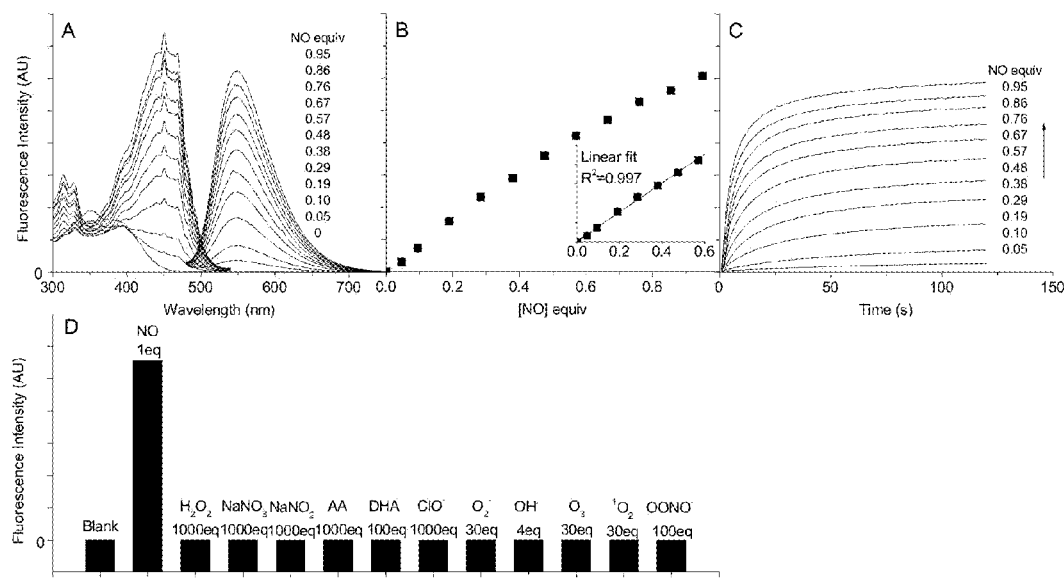
FIG. 4A is an overlay of the excitation spectra ($\lambda_{em}$=550 nm) and emission spectra (with $\lambda_{ex}$=470 nm) when different aliquots of NO are added to a $NO_{550}$ solution (50 μM) in PBS buffer containing 20% DMSO. Spectra were collected 2 minutes after NO addition.
FIG. 4B is a graph depicting the enhancement of the fluorescence intensity ($\lambda_{ex}$=470 nm and $\lambda_{em}$=550 nm) upon NO addition over a period of 2 minutes.
FIG. 4C is a graph depicting the kinetics profile of the reaction between $NO_{550}$ ($\lambda_{ex}$=470 nm and $\lambda_{em}$=550 nm).
FIG. 4D is a chart depicting the fluorescence intensity of solution containing $NO_{550}$ (50 μM) after addition of following substances: NO, and various equivalent of $H_2O_2$, $NO_3^-$, $NO_2^-$, ascorbic acid (AA), dehydroascorbic acid (DHA), $ClO^-$, $O_2$, $OH.$, $O_3$, $^1O_2$, and $ONOO^-$.

Due to the limited aqueous solubility of $NO_{550}$, 20% DMSO in PBS buffer (50 mM at pH=7.4 with 150 mM NaCl) was used for spectroscopic studies. $NO_{550}$ displays an absorption band centered at 352 nm which tails to 450 nm (FIG. 3), and shows no fluorescence in aqueous media. It is believed that the lack of emission is likely due to a combination of PET from the 3'-dimethylaminophenyl ring and rotational deactivation along the aryl-aryl single bond. As an aliquot of the NO stock solution (1.9 mM in de-ionized $H_2O$) was added, an absorption band centered at 450 nm appeared immediately while that at 352 nm diminished. Concomitantly, an emission band centered at 550 nm (with a broad maximum excitation ranging from 440 nm to 470 nm) appeared from a dark background (FIG. 4A), and was identical to that for purified $AZO_{550}$. A completely dark background from which a bright signal appears in response to NO is unique for this strategy. A fluorescence enhancement over 1500 fold (FIG. 5) was observed compared to a ca. 200 fold enhancement with DAF-2 DA (calculated with published photophysical parameters). Excellent linear correlation ($R^2$=0.995) was found between the fluorescence enhancement and the NO concentration (FIG. 4B). The kinetics of the reaction of $NO_{550}$ with NO was studied via time-based fluorescence ($\lambda_{ex}$=470 nm and $\lambda_{em}$=550 nm). It took approximately 20 seconds for various aliquots of NO to complete the fast phase of the reaction, which accounts for 80% of overall signal enhancement. (FIG. 4C). This fast kinetic profile allows for good temporal resolution in cellular imaging studies. Unlike the existing fluorescein-based probes, the fluorescence of $AZO_{550}$ was independent of pH from 4.5 to 9 (FIG. 6), which is advantageous because different cells or even the different compartments in the same cell may have different pH values. The molar absorptivity and quantum yield of $AZO_{550}$ were 4000 $M^{-1}cm^{-1}$ at 470 nm and 0.11 respectively in 20% DMSO. The φ is likely higher in the lipophilic regions of cells where NO is released. The limit of detection (LOD, when the signal equals three times the noise) was estimated to be around 30 nM in 20% DMSO (FIG. 4B). A wide array of possible competitive reactive oxygen or nitrogen species, and others analytes at up to 1000 fold excess: $H_2O_2$, $NO_3^-$, $NO_2^-$, ascorbic acid (AA), dehydroascorbic acid (DHA), $ClO^-$, $O_2^-$, $OH·$, $O_3$, $^1O_2$, and $ONOO^-$ (FIG. 4D) were also screened. None of these species induced any interfering signals due to our unique detection mechanism.

$NO_{550}$ was Used to Image NO in NSA and PC12 Cell Lines $NO_{550}$ was used to visualize both endogenously produced NO, and exogenously supplied NO by an donor (sodium nitroprosside, SNP) in the culture of two cells types: neonatal spinal astrocytes and the pheochromocytoma-derived, PC12 cell line, which is commonly used as a model for neurons. Both cell types have been previously reported to produce NO. The $NO_{550}$ appears to enter the cytoplasm in both cell types, but does not cross into the nuclei. The viability of PC12 cells and astrocytes when incubated with the NO dye was evaluated by measuring their metabolic activity after 30 minutes. No differences were observed between cells incubated with the dye and controls.

Several in vitro experiments were performed to confirm that $NO_{550}$ responded to NO in a biological context. Astrocytes were stimulated with interleukin-1β (IL-1β) and interferon-γ (IFN-γ) to induce NO production and then incubated with $NO_{550}$ for 15 minutes. A stronger fluorescence signal was observed in the astrocytes that displayed the "spindle" phenotype, induced by cytokine stimulation, when compared to those exhibiting a flattened spread phenotype (FIG. 7A). This agrees with previous reports that "spindle" phenotypes produce higher levels of NO when induced by cytokines. Longer incubation times (>15 minutes) with $NO_{550}$ did not lead to enhanced fluorescence, indicating that the probe had reached a diffusive equilibrium in the cells. Upon addition of an NO donor (sodium nitroprusside, SNP) to cell cultures, a notable increase in fluorescence of both astrocytic phenotypes occurred (FIG. 7B, data with PC12 cells not shown). A quantitative comparison of data from FIGS. 7A and 7B showed a measurably larger fluorescence increase when SNP is added to the cell culture. (FIG. 7E)

Figure 8:
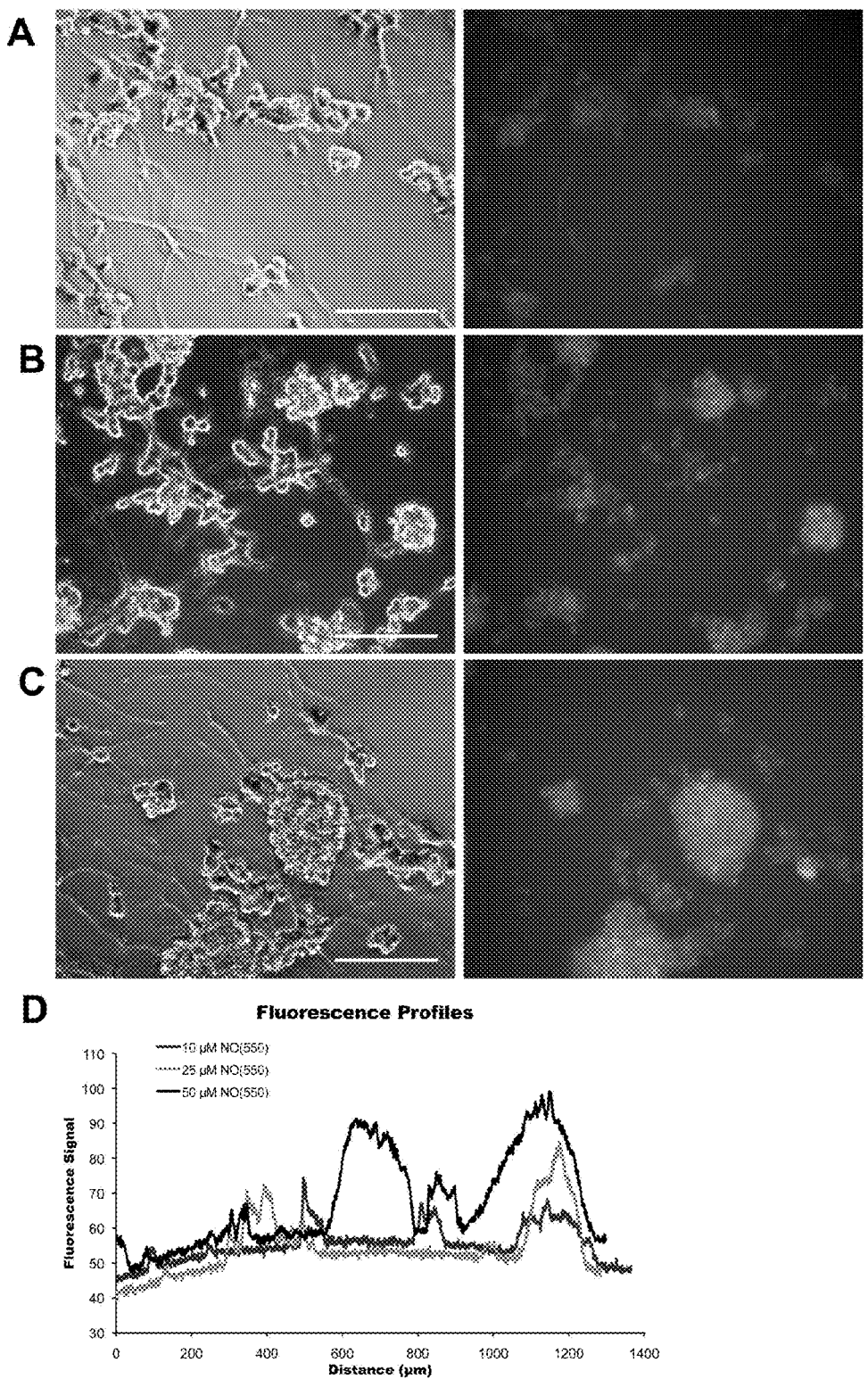

$NO_{550}$ was also compared to a commercially available NO probe, DAF-2 DA. $NO_{550}$ yielded far less background fluorescence than DAF-2 DA when incubated with PC12 cells and subsequently imaged (FIGS. 7C,D,F). This result is not unexpected, because DAF-2 itself has background-fluorescence, and it reacts with dehydroascorbic acid, which significantly contributes to the background. An even higher background was observed when DAR-4M AM was used (data not shown), which agrees with its elevated reactivity toward DHA compared to DAF-2 DA. In addition, a higher concentration of $NO_{550}$ (up to 50 μM) could be used to further increase the signal-to-background ratio in the images (FIG. 8). $NO_{550}$ was not observed to permeate the nuclear membrane, while fluorescence was observed in the cell nuclei in cultures incubated with DAF-2 DA. The fluorescence signal from $NO_{550}$ was concentrated around the nuclei, when incubated with both cell lines. This further confirms the utility of $NO_{550}$ because NO synthase associates with the Golgi bodies near the nucleus in both cytokine-stimulated astrocytes and nerve growth factor (NGF) stimulated PC12 cells. Thus it is reasonable to expect that more NO is present in these high density areas of NO synthase.

Synthetic Scheme of NO550 and AZO550

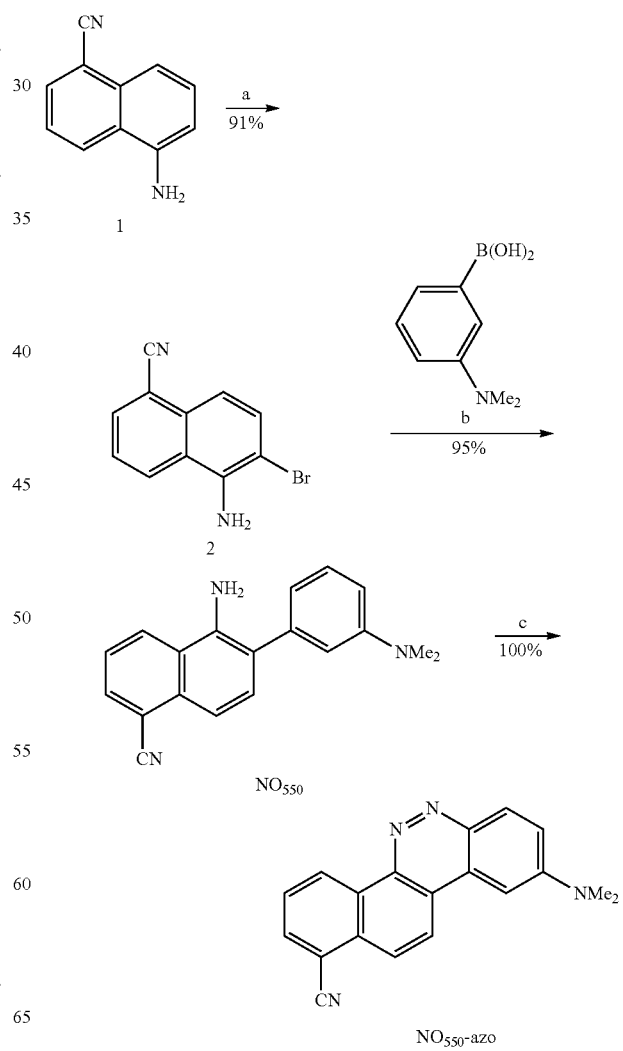

Compound 1 was synthesized following literature procedures. Regioselective bromination of 1 (0.82 g) using NBS (0.91 g, 1.0 eq) yielded compound 2 (1.1 g, 91%) by stirring with a catalytic amount of normal phase silica gel (30 mg) in $CH_3CN$ (100 mL) for 16 hrs at room temperature. The reaction was not protected from light or air. The crude product after filtration and evaporation was purified by flash column using $CH_2Cl_2$ as eluent. $^1$HNMR (300 MHz, DMSO-$d_6$) δ 8.59 (d, 1H, J=8.7 Hz), 8.10 (d, 1H, J=7.2 Hz), 7.72 (d, 1H, J=8.7 Hz), 7.22 (d, 1H, J=9.0 Hz), 7.57 (dd, 1H, J=8.4, 7.5 Hz). $^{13}$CNMR (300 MHz, DMSO-$d_6$) δ 142.7, 133.3, 133.1, 131.9, 128.5, 124.3, 122.3, 117.8, 112.4, 108.8, 102.5. HRMS m/z=246.9871 (M+H$^+$), calculated 246.9871.

The mixer containing 2 (95 mg), 3-dimethylaminophenylboronic acid (62 mg, 1.0 eq), Pd(PPh$_3$)$_4$ (10 mg, 0.02 eq) and Na$_2$CO$_3$ (320 mg, 8.0 eq) in 8 mL of H$_2$O:EtOH:Benzene (v/v 3:3:10) was refluxed for 24 hrs under argon atmosphere. The reaction mixture was poured into H$_2$O and extracted with $CH_2Cl_2$. The crude product after evaporation was purified by flash column using $CH_2Cl_2$ to yield NO$_{550}$ (106 mg, 99%). $^1$HNMR (400 MHz, CDCl$_3$) δ 8.13 (d, 1H, J=8.8 Hz), 7.89 (dd, 1H, J=7.2, 1.2 Hz), 7.73 (dd, 1H, J=8.4, 1.2 Hz), 7.54 (d, 1H, J=8.4 Hz), 7.50 (dd, 1H, J=8.8, 7.2 Hz), 7.38 (dd, 1H, J=7.6, 7.6 Hz), 7.26 (s, 1H), 6.84-6.77 (m, 3H), 4.48 (s, 2H), 3.008 (s, 6H). $^{13}$CNMR (400 MHz, CDCl$_3$) δ 151.7, 140.5, 140.2, 133.4, 133.0, 132.1, 130.5, 127.3, 125.4, 124.5, 123.9. 118.9, 118.0, 115.8, 113.9, 112.4, 111.1, 41.2. HRMS m/z=288.1500 (M+H$^+$), calculated 288.1495.

Bubbling NO gas into a $CH_2Cl_2$ solution containing NO$_{550}$ (13.5 mg) at room temperature for 5 minutes yielded AZO$_{550}$ (14.0 mg, 100%) after evaporation and flash column by $CH_2Cl_2$ with 1% ammonia saturated MeOH. $^1$HNMR (600 MHz, DMSO-$d_6$) δ 9.86 (d, 1H, J=7.8 Hz), 8.95 (d, 1H, J=9.6 Hz), 8.42 (d, 1H, J=9.6 Hz), 8.37 (dd, 1H, J=7.2, 1.2 Hz), 8.28 (dd, 1H, J=9.0, 1.0 Hz), 8.00 (dd, 1H, J=8.4, 7.2 Hz), 7.60 (dd, 1H, J=9.3, 2.4 Hz), 7.56 (d, 1H, J=2.4 Hz), 3.25 (s, 6H). $^{13}$CNMR (600 MHz, DMSO-$d_6$) δ 151.9, 142.0, 140.0, 134.3, 131.7, 131.6, 130.3, 129.1, 127.7, 125.8, 123.7, 123.0, 118.7, 118.6, 117.5, 109.2, 97.6, 40.1. HRMS m/z=344.1147 (M+H$^+$), calculated 344.1148.

Materials and Methods

The $^1$HNMR and $^{13}$CNMR spectra were recorded on Varian Unity Plus 300, Varian MERCURY 400 and Varian NOVA 600 spectrometers. High-resolution MS (HRMS) spectra were obtained a Micromass Autospec Ultima mass spectrometer with a double focusing magnetic sector. UV-Vis spectra were recorded on a Beckman Coulter DU 800 UV-Vis spectrophotometer. Fluorescence spectra were recorded on a PTI QuantaMaster™ intensity based spectrofluorometer equipped with 814 photomultiplier detection system (V=1000 volts). The excitation and emission slits were set at 1.0 mm. All titrations were performed at aerobic conditions.

Purified neonatal astrocytes were obtained from P0 rat spinal cords (Sprague Dawley, Charles Rivers, Wilmington, Mass.). All animal work was performed in accordance with the Institutional Animal Care and Use Committee at the University of Texas at Austin. Astrocytes were cultured in DMEM (Sigma-Aldrich, St. Louis, Mo.) with 10% fetal bovine serum (Invitrogen, Carlsbad, Calif.) and 1% penicillin/streptomycin/amphotericin B (Sigma-Aldrich). Astrocyte cultures were immunostained against glial fibrillary acidic protein (GFAP, Abcam, Cambridge, Mass.) using standard procedures to confirm phenotype and used in experiments from passages 2-5. To induce NO production, cells were stimulated with 200 U mL$^{-1}$ interferon-γ (IFN-γ) and 10 ng mL$^{-1}$ interleukin-1β (IL-1β) for 24-48 h. PC12 cells were cultured in F12K/DMEM (Sigma-Aldrich) with 7.5% heat-inactivated house serum, 2.5% fetal bovine serum, and 1% penicillin/streptomycin/amphotericin B. To induce NO production, PC12 cells were stimulated with 50 ng mL$^{-1}$ nerve growth factor (NGF) for 8-10 days. Viability of cells incubated in NO$_{550}$ was evaluated using a CellTiter Glo luminescence assay according to the manufacturer's instructions (Promega, Madison, Wis.).

Immediately prior to NO imaging, cells were rinsed in Dulbecco's phosphate-buffered saline, pH 7.2 (PBS; Sigma-Aldrich) and kept in PBS during the imaging procedure. The 10 μM of NO$_{550}$ or 10 μM of diaminofluorescein-2 (DAF-2 DA; Sigma-Aldrich); both diluted from stock in DMSO) was incubated with cells for approximately 15 min. at 37° C. before imaging. In some cases cells were incubated with 1 mM sodium nitroprusside (Sigma-Aldrich) for 15 minutes before an additional rinse in PBS and incubation with NO$_{550}$. Phase contrasts and fluorescence images were acquired using a wide-field fluorescence microscope (IX70; Olympus; Center Valley, Pa.) equipped with a standard fluorescein filter cube set (Olympus) and a 20× (0.5 numerical aperture) objective (UPLFLN-PH, Olympus). Line plots of fluorescence signal were constructed using ImageJ software (NIH, Bethesda, Md.).

The nitric oxide (NO) stock solution in de-ionized water was prepared by bubbling NO into deoxygenated de-ionized water for 15 minutes. (Ouyang, J. et al. A novel fluorescent probe for the detection of nitric oxide in vitro and in vivo. *Free Radic. Biol. Med.* 45, 1426-1436 (2008)). Superoxide radical anion (O$_2^-$) was from KO$_2$. Hydroxyl radical (HO.) was generated from H$_2$O$_2$ and FeSO$_4$. Singlet oxygen ($^1$O$_2$) was generated from ClO$^-$ and H$_2$O$_2$. Peroxynitrite was generated from amyl nitrite and H$_2$O$_2$ following literature procedures. (Uppu, R. M. & Pryor, W. A. Synthesis of peroxynitrite in a two-phase system using isoamyl nitrite and hydrogen peroxide. *Anal. Biochem.* 236, 242-249, (1996)).

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

REFERENCES

1. *Nitric Oxide*, edited by Bernd Mayer, Handbook of Experimental Pharmacology, Vol. 143, (Springer: Berlin, 2000).
2. *Nitric Oxide Biology and pathobiology*, edited by Louis J. Ignarro (Academic Press, San Diego, 2000).
3. Nagano, T. & Yoshimura, T. Bioimaging of nitric oxide. *Chem. Rev.* 102, 1235-1269 (2002).
4. Hetrick, E. M. & Schoenfisch, M. H. Analytical chemistry of nitric oxide. *Annu. Rev. Anal. Chem.* 2, 409-433 (2009).
5. Kojima, H. et al. Detection and imaging of nitric oxide with novel fluorescent indicators: diaminofluoresceins. *Anal. Chem.* 70, 2446-2453 (1998).
6. Heiduschka, P. & Thanos, S, NO production during neuronal cell death can be directly assessed by a chemical reaction in vivo. *NeuroReport* 9, 4051-4057 (1998).
7. Meineke, P., Rauen, U., de Groot, H., Korth, H.-G. & Sustmann, R. Cheletropic traps for the fluorescence spectroscopic detection of nitric oxide (nitrogen monoxide) in biological systems. *Chem. Eur. J.* 5, 1738-1747 (1999).
8. Kojima, H. et al. Bioimaging of nitric oxide with fluorescent indicators based on rhodamine chromophore. *Anal. Chem.* 73, 1967-1973 (2001).
9. Gabe, Y., Urano, Y., Kikuchi, K., Kojima, H. & Nagano, T. Highly sensitive fluorescence probes for nitric oxide based on boron dipyrromethene chromophore-rational design of potentially useful bioimaging fluorescence probe. *J. Am. Chem. Soc.* 126, 3357-3367 (2004).
10. Sasaki, E. et al. Highly sensitive near-infrared fluorescent probes for nitric oxide and their application to isolated organs. *J. Am. Chem. Soc.* 127, 3684-3685 (2005).
11. Lim, M. H., Xu, D. & Lippard, S. J. Visualization of nitric oxide in living cells by a copper-based fluorescent probe. *Nature Chem. Biol.* 2, 375-380 (2006).
12. Lim, M. H. et al. Direct nitric oxide detection in aqueous solution by copper(II) fluorescein complexes. *J. Am. Chem. Soc.* 128, 14363-14373 (2006).
13. Zheng, H., Shang, G.-Q., Yang, S.-Y., Gao, X. & Xu, J.-G. Fluorogenic and chromogenic rhodamine spirolactam based probe for nitric oxide by spiro ring opening reaction. *Org. Lett.* 10, 2357-2360 (2008).
14. Wang, S., Han, M.-Y. & Huang, D. Nitric oxide switches on the photoluminescence of molecularly engineered quantum dots. *J. Am. Chem. Soc.* 131, 11692-11694 (2009).
15. Kim, J.-H. et al. The rational design of nitric oxide selectivity in single-walled carbon nanotube near-infrared fluorescence sensors for biological detection. *Nature Chem.* 1, 473-481 (2009).
16. Jourd'heuil, D. Increased nitric oxide-dependent nitrosylation of 4,5-diaminofluorescein by oxidants: implications for the measurement of intracellular nitric oxide. *Free Radic. Biol. Med.* 33, 676-684 (2002).
17. Roychowdhury, S., Luthe, A., Keilhoff, G., Wolf, G. & Horn, T. F. W. Oxidative stress in glial cultures: Detection by DAF-2 fluorescence used as a tool to measure peroxynitrite rather than nitric oxide. *Glia* 38, 103-114 (2002).
18. Wardman, P. Fluorescent and luminescent probes for measurement of oxidative and nitrosative species in cells and tissues: progress, pitfalls, and prospects. *Free Radic. Biol. Med.* 43, 995-1022 (2007).
19. Zhang, X. et al. Interfering with nitric oxide measurements: 4,5-diaminofluorescein reacts with dehydroascorbic acid and ascorbic acid. *J. Biol. Chem.* 277, 48472-48478 (2002).
20. Ye, X., Rubakhin, S. S. & Sweedler, J. V. Simultaneous nitric oxide and dehydroascorbic acid imaging by combing diaminofluoresceins and diaminorhodamines. *J. Neurosci. Methods.* 168, 373-382 (2008).
21. Lim, M. H. & Lippard, S. J. Metal-based turn-on fluorescent probes for sensing nitric oxide. *Acc. Chem. Soc.* 40, 41-51 (2007).
22. Hartung, J. Organic radical reactions associated with nitrogen monoxide. *Chem. Rev.* 109, 4500-4517 (2009).
23. Lee, S. C., Dickson, D. W., Liu, W. & Brosnan. C. F. Induction of nitric oxide synthase activity in human astrocytes by IL-1β and IFN-γ. *J. Neuroimmunol.* 46. 19-24 (1993).
24. Liu, B. & Neufeld. A. H. Expression of nitric oxide synthase-2 (NOS-2) in reactive astrocytes of the human glaucomatous optic nerve head. *Glia* 30, 178-186 (2000).
25. Zhao, M. L., Liu, J. S. H., He, D., Dickson, D. W. & Lee. S. C. Inducible nitric oxide synthase expression is selectively induced in astrocytes isolated from adult human brain. *Brain Res.* 813, 402-405 (1998).

What is claimed is:

1. A nitric oxide probe comprising a compound represented by the following Formula II:

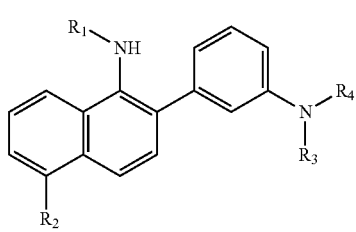

Formula II wherein $R_1$ is an alkyl group or H, $R_2$ is H, CN, $SO_3^-$, sulfamoyl, alkyl substituted sulfamoyls, $COO^-$, carbamoyl, alkyl substituted carbamoyls, $R_3$ is an alkyl group, and $R_4$ is an alkyl group.

2. The nitric oxide probe of claim 1 wherein $R_1$ is H, —$R_2$ is H or CN, $R_3$ is a methyl group, and $R_4$ is a methyl group.

3. A method of detecting the presence of nitric oxide in a sample comprising:
    contacting a sample with the nitric oxide probe of claim 1; and
    detecting emitted fluorescence from the nitric oxide probe, wherein the emitted fluorescence indicates the presence of nitric oxide in the sample.

* * * * *